(12) United States Patent
Hernandez et al.

(10) Patent No.: US 7,314,634 B2
(45) Date of Patent: Jan. 1, 2008

(54) USE OF POLYPHENOLS TO TREAT SKIN CONDITIONS

(76) Inventors: Steven Hernandez, 5200 New Horizons Blvd., Amityville, NY (US) 11701; Burt Shaffer, 5200 New Horizons Blvd., Amityville, NY (US) 11701

( * ) Notice: Subject to any disclaimer, the term of this patent is extended or adjusted under 35 U.S.C. 154(b) by 0 days.

(21) Appl. No.: 10/341,101

(22) Filed: Jan. 13, 2003

(65) Prior Publication Data

US 2003/0175234 A1    Sep. 18, 2003

Related U.S. Application Data

(60) Provisional application No. 60/359,171, filed on Feb. 22, 2002.

(51) Int. Cl.
*A61K 8/02* (2006.01)
*A61K 6/00* (2006.01)
*A61K 31/35* (2006.01)
*A01N 65/00* (2006.01)

(52) U.S. Cl. .................. 424/401; 424/400; 424/725; 424/729; 514/456; 514/859; 514/887

(58) Field of Classification Search ............... 424/400, 424/401, 725, 729; 514/456, 859, 887
See application file for complete search history.

(56) References Cited

U.S. PATENT DOCUMENTS

| | | | | |
|---|---|---|---|---|
| 5,043,323 | A * | 8/1991 | Bombardelli et al. | 514/25 |
| 5,750,563 | A * | 5/1998 | Honda | 514/460 |
| 5,843,411 | A | 12/1998 | Hernandez et al. | 424/59 |
| 6,110,477 | A | 8/2000 | Hernandez et al. | 424/401 |
| 6,316,012 | B1 | 11/2001 | N'Guyen et al. | 424/401 |
| 6,337,320 | B1 * | 1/2002 | Hersh et al. | 514/18 |
| 6,399,046 | B1 | 6/2002 | Schonrock et al. | 424/59 |
| 6,426,081 | B1 * | 7/2002 | Chong | 424/401 |
| 6,455,057 | B1 | 9/2002 | Barrett et al. | 424/401 |
| 6,551,602 | B1 | 4/2003 | Barrett et al. | 424/401 |
| 6,605,296 | B1 | 8/2003 | Stuckler | 424/439 |
| 6,630,163 | B1 * | 10/2003 | Murad | 424/464 |
| 6,680,062 | B2 | 1/2004 | Muizzuddin et al. | 424/401 |

OTHER PUBLICATIONS

Santosh K. Katiyar, PhD; Archives of Dermatology, Nihal Ahmad, PhD; Hasan Mukhtar, PhD "Green Tea and Skin", Aug. 2000 vol. 136 No. 8.

Masami Uehara, MD; Hisashi Sugiura, MD; Kensei Sakurai, MD A Trial of Oolong Tea in the Management of Recalcitrant Atopic Dermatitis, "Archives of Dermatology", Jan. 2001 vol. 137 No. 1.

Gary S. Wood, MD, "Archives of Dermatology", "Green Tea Whats Brewing?", Aug. 2000 vol. 136 p. 1051.

Sheldon R. Pinnell, MD Durham, North Carolina, "J Am Acad Dermatol" "Cutaneous photodamage, oxidative stress, and topical antioxidant protection", Jan. 2003 vol. 48, No. 1 p. 1-19.

Yao-Ping Lu, You-Rong-Lou, Jian-Guo Xie, Qing-Yun Peng, Jie Liao, Chung S. Yang, Mou-Tuan Huang, and Allan H. Conney, "Ssan Lehman Cullman Laboratory for Cancer Research, Department of Chemical Biology, Ernest Mario School of Pharmacy, Rutgers, State University of New Jersey, Piscataway, NJ 08854-8020" "Topical applications of caffeine or (-)-epigallocatechin gallate (EGCG) inhibit carcinogenesis and selectively increase apoptosis in UVB-induced skin tumors in mice" PNAS Sep. 17, 2002, vol. 99, No. 19/ 12455-12460.

Helen L. Gensler, Barbara N. Timmermann, Susanne Valcic, Gerald A. Wachter, Robert Dorr, Katerina Dvorakova and David S. Alberts, "Nutrition and Cancer 1996", "Prevention of Photocarcinogenesis by Topical Administration of Pure Epigallocatechin Gallate Isolated From Green Tea", vol. 26, No. 3, pp. 325-335.

Santosh K. Katiyar, Anjana Challa, Thomas S. McCormick, Kevin D. Cooper and Hasan Mukhtar, "Carcinogenesis", "Prevention of UVB-induced immunosuppression in mice by the green tea polyphenol (-)-epigallocatechin-3-gallate may be associated with alterations in IL-10 and IL-12 production", vol. 20, No. 11, pp. 2117-2124, 1999.

* cited by examiner

*Primary Examiner*—Sreeni Padmanabhan
*Assistant Examiner*—Marina Lamm
(74) *Attorney, Agent, or Firm*—Alfred M. Walker

(57) ABSTRACT

A composition is provided to treat and/or prevent for treating skin conditions including fine lines and wrinkles, acne rosacea, surface irregularities of the skin and hyper-pigmentation melasma of the skin, which includes use of a topically applied composition such as an ointment, lotion, cream, serum, gel or pad applied formulation, containing an effective amount of polyphenols, such as green tea based polyphenols, including but not limited to catechins, such as epigallocatechin gallate (EGCG), epigallocatechin (EGC), epicathechin 3-gallate (ECG) and epicatechin (EC). The formulation is preferably composed of 90 percent polyphenol isolates, derived from green tea with potent antioxidant properties, to assist in minimizing free-radical induced skin damage.

10 Claims, No Drawings

USE OF POLYPHENOLS TO TREAT SKIN CONDITIONS

RELATED APPLICATIONS

This application is based upon provisional application No. 60/359,171, filed Feb. 22, 2002.

FIELD OF THE INVENTION

The present invention relates to topical treatments for fine lines and wrinkles, acne rosacea, or surface irregularities of the skin, as well for a topically applied as a skin bleaching agent for reduction of hyper-pigmentation melasma.

BACKGROUND OF THE INVENTION

Overexposure to the sun and other toxic free radical sources and irritants induces skin damage, resulting in a variety of disfiguring skin conditions. Among these skin conditions, wrinkles and fine lines are caused by sun damage and aging. Wrinkles of the skin are either deep furrows and creases or fine lines. Wrinkles can occur on any part of the body, but especially where sun exposure is greatest, such as on the face, neck, forearms and hands.

Acne is a blemishing skin condition displayed as pimples, blackheads, whiteheads, skin cysts and other blemishes in areas which are concentrated with a preponderance of skin oils, such as on the face, chest or back. If untreated, acne can result in deep surface scarring irregularities.

The aforementioned skin conditions are typically treated by topical application of salicylic acid or alpha hydroxy acids, either alone or in combination with drying agents such as benzoyl peroxide. In the case of acute acne, the treatment regimen includes oral ingestion of antibiotics.

Acne rosacea is a specialized skin condition causing persistent redness over the forehead, chin, cheeks and nose. Acne rosacea is treated with anti-inflammatories, such as metronitizole USP, such as METROGEL® or NORITATE®.

Furthermore, melasma is a skin condition where the skin is discretely spotted with excessive hyper-pigmentation in selected areas of the skin, resulting in prominent blotches on the skin.

Heretofore, it has been difficult to treat these skin conditions with existing treatment regimens. Therefore, there is a long felt need to provide a tolerable yet effective treatment for the aforementioned skin abnormalities. In Applicant's issued U.S. Pat. Nos. 5,843,411 and 6,110,477, it has been shown that anti-oxidants such as ascorbic acid are effective for treating certain conditions, but ascorbic acid is inherently unstable and needs to be stabilized before its anti-oxidant proportion can be effectively utilized. Therefore, there is a need for a stable anti-oxidant for treating certain skin conditions.

Certain plants such as green tea, are composed of a high content of polyphenols, which are bioflavonoids that have been shown to have anti-oxidant properties. Green tea contains specific polyphenols that are commonly known as catechins, which possess highly potent antioxidant characteristics. The most noted preventive catechin in green tea polyphenols is epigallocatechin gallate (EGCG). Other catechins found in green tea are epigallocatechin (EGC), epicatechin 3-gallate (ECG) and epicatechin (EC).

It has been demonstrated in scientific literature that polyphenols, such as from green tea, are antioxidants, with anti-inflammatory and anticarcinogenic properties, as noted in *Archives of Dermatology* 2000; 136:989-994. Research has shown that green tea, especially its component epigallocatechin gallate, can block Ultraviolet-B (UV-B) light ray induced leukocyte infiltration in mouse and human skin, as noted in *Carcinogenesis* 1999, 2117-2124, and in *Nutrition and Cancer* 1996, 26(3); 325-335.

However it is not known to provide a topical composition for treatment of fine lines and wrinkles, acne rosacea, surface irregularities of the skin and melasma hyper-pigmentation of the skin, wherein the composition includes green tea extract and its polyphenol components, such as, for example, catechins.

OBJECTS OF THE INVENTION

It is therefore an object of the present invention to reduce skin fine lines and wrinkles, acne rosacea, surface irregularities of the skin and hyper-pigmentation melasma of the skin.

It is yet another object of the present invention to provide a skin treatment composition useful in the treatment of fine lines and wrinkles, acne rosacea, surface irregularities of the skin and melasma hyper-pigmentation of the skin.

It is also an object of the present invention to improve over the disadvantages of the prior art.

BRIEF SUMMARY OF THE INVENTION

The present invention comprises a method for treating skin conditions including fine lines and wrinkles, acne rosacea, surface irregularities of the skin and hyper-pigmentation melasma of the skin, which includes use of a topically applied composition such as an ointment, lotion, cream or serum, containing an effective amount of polyphenols or polyphenols from green tea, including but not limited to catechins, such as epigallocatechin gallate (EGCG), epigallocatechin (EGC), epicathechin 3-gallate (ECG) and epicatechin (EC).

The formulation is preferably composed of 90 percent polyphenol isolates, derived from green tea with potent antioxidant properties, to assist in minimizing free-radical induced skin damage.

In one embodiment, the formulation is a lightweight, fast absorbing water soluble serum formulation also containing the humectant hyaluronic acid to deliver enhanced moisturization and improved texture, tone and overall skin appearance.

In another embodiment for a cream formulation, there is provided an emollient, rich, water soluble cream containing hyaluronic acid and a soy phospholipid complex to achieve smoother, silkier, softer and more radiant looking skin.

The formulations of the present invention are non-comedogenic in that they do not tend to produce or aggravate skin acne. Moreover, they can be incorporated into existing prescription and over the counter skin care regimens.

EXAMPLES

A serum of the present invention was shown in the a medical case profile to be therapeutically effective in treatment of fine lines and wrinkles around the eyes, skin redness and a skin surface irregularity of large skin pores, where the serum was applied twice daily, in a morning and evening regimen, for a thirty day period with positive results, preventing further development of these skin conditions.

In addition, the formulations of the present invention have been found in clinical studies to be effective in reduction of hyper-pigmentation melasma of the skin.

DETAILED DESCRIPTION OF THE INVENTION

In accordance with the present invention, a method is provided for the treatment of skin conditions including fine lines and wrinkles, acne rosacea and surface irregularities of the skin, as well as hyper-pigmentation melasma of the skin, which includes the steps of using a topically applied composition such as an ointment, lotion, cream, serum, gel or pad applied formulation containing an effective amount of polyphenols, such as green tea based polyphenols, including but not limited to catechins, such as epigallocatechin gallate (EGCG), epigallocatechin (EGC), epicathechin 3-gallate (ECG), and epicatechin (EC), or combinations thereof.

The formulation is preferably composed of 90 percent polyphenol isolates, derived from green tea with potent antioxidant properties, to assist in minimizing free-radical induced skin damage.

For example, the serum formulation preferable includes 90% polyphenol green tea extract in an amount of 0.05-10 percent, preferably about 0.25 percent, by weight of the total composition.

In addition, the cream formulation preferably includes 90% polyphenol green tea extract in an amount of from about 0.05 to about 10 percent, preferably about 0.25 percent.

In one embodiment, the formulation is a lightweight, fast absorbing water soluble serum formulation also containing the humectant hyaluronic acid, to deliver enhanced moisturization and improved texture, tone and overall skin appearance.

In another embodiment for a cream formulation, there is provided an emollient, rich, water soluble cream containing hyaluronic acid and a soy phospholipid complex to achieve smoother, silkier, softer and more radiant looking skin.

Each of these components has been shown in the medical literature to have effects that promote healing by a variety of mechanisms.

The following examples illustrate typical topically applied skin care products, which can be prepared using conventional procedures, from the following ingredients with ranges of acceptable percentages shown by weight, and typical preferred percentage by weight shown.

The formulations are illustrative only:

| Ingredient | % Range | % Preferred |
|---|---|---|
| 1. Cream | | |
| Water | 0-99.95 | 87.57 |
| Carbomer | 0-5 | 0.40 |
| Methylparaben | 0-1 | 0.10 |
| Tetrasodium EDTA | 0-1 | 0.12 |
| Triethanolamine | 0-5 | 0.50 |
| Lecithin | 0-25 | 5.00 |
| Behenyl Alcohol | 0-25 | 1.00 |
| Stearic Acid | 0-25 | 0.10 |
| Sodium Hyaluronate | 0-5 | 0.01 |
| Glyceryl Stearate | 0-25 | 1.00 |
| C12-16 Alcohols | 0-25 | 1.00 |
| Germall II | 0-1.0 | 0.30 |
| Palmitic Acid | 0-25 | 1.00 |
| Bisabolol | 0-10 | 0.10 |
| Polysorbate-20 | 0-25 | 0.20 |
| 90% Polyphenol Green Tea Ext. | 0.05-10 | 0.25 |
| Cucumber Extract | 0-99.95 | 1.00 |
| Chamomile Extract | 0-99.95 | 0.10 |
| Soy Phospholipids | 0-25 | 0.25 |
| 2. Serum | | |
| Water | 0-99.95 | 96.92 |
| Carbomer | 0-5 | 0.40 |
| Methylparaben | 0-1 | 0.10 |
| Tetrasodium EDTA | 0-1 | 0.12 |
| Triethanolamine | 0-5 | 0.50 |
| Sodium Hyaluronate | 0-5 | 0.01 |
| Germall II | 0-1.0 | 0.30 |
| Bisabolol | 0-10 | 0.10 |
| Polysorbate-20 | 0-25 | 0.20 |
| 90% Polyphenol Green Tea Ext. | 0.05-10 | 0.25 |
| Cucumber Extract | 0-99.95 | 1.00 |
| Chamomile Extract | 0-99.95 | 0.10 |

In general, the treatment composition suitable for use in accordance with the invention may be applied in any dermatological acceptable vehicle such as a serum, cream, ointment, gel, lotion, or pad applied formulation, which may or may not be emulsified and may contain ingredients to improve, modify, or stabilize the formulation physically or cosmetically. Other suitable formulations will be apparent to those skilled in the art.

Other changes to the present invention may be made without departing from the spirit or scope thereof, in accordance with the accompanying Claims.

We claim:

1. A method of treating fine lines and wrinkles in skin by topical application, consisting essentially of the steps of:
   a. preparing a composition for topical application containing a therapeutically effective amount of at least one polyphenol derived from green tea dispersed in a suitable dermatologically acceptable vehicle, said composition comprising a cream having the following ingredients with said ingredients being provided in the below listed percentage by weight:

| Ingredient | % |
|---|---|
| Water | 87.57 |
| Carbomer | 0.40 |
| Methylparaben | 0.10 |
| Tetrasodium EDTA | 0.12 |
| Triethanolamine | 0.50 |
| Lecithin | 5.00 |
| Behenyl Alcohol | 1.00 |
| Stearic Acid | 0.10 |
| Sodium Hyaluronate | 0.01 |
| Glyceryl Stearate | 1.00 |
| C12-16 Alcohols | 1.00 |
| Germall II | 0.30 |
| Palmitic Acid | 1.00 |
| Bisabolol | 0.10 |
| Polysorbate 20 | 0.20 |
| 90% Polyphenol Green Tea Extract | 0.25 |
| Cucumber Extract | 1.00 |
| Chamomile Extract | 0.10 |
| Soy Phospholipids | 0.25; | b. topically applying said composition to the skin to be treated; and
   c. periodically repeating said topical application.

2. A method of treating fine lines and wrinkles in skin by topical application, consisting essentially of the steps of:
   a. preparing a composition for topical application containing a therapeutically effective amount of at least one polyphenol derived from green tea dispersed in a suitable dermatologically acceptable vehicle, said composition comprising a serum having the following ingredients present in the below-listed percentage by weight:

| Ingredient | % |
| --- | --- |
| Water | 96.92 |
| Carbomer | 0.40 |
| Methylparaben | 0.10 |
| Tetrasodium EDTA | 0.12 |
| Triethanolamine | 0.50 |
| Sodium Hyaluronate | 0.01 |
| Germall II | 0.30 |
| Bisabolol | 0.10 |
| Polysorbate - 20 | 0.20 |
| 90% Polyphenol Green Tea Extract | 0.25 |
| Cucumber Extract | 1.00 |
| Chamomile Extract | 0.10; | b. topically applying said composition to the skin to be treated; and
   c. periodically repeating said topical application.

3. A method of treating acne rosacca of the skin by topical application, consisting essentially of the steps of:
   a. preparing a composition for topical application containing a therapeutically effective amount of at least one polyphenol derived from green tea dispersed in a suitable dermatologically acceptable vehicle, said composition comprising a cream having the following ingredients present in the below-listed percentage by weight:

| Ingredient | % |
| --- | --- |
| Water | 87.57 |
| Carbomer | 0.40 |
| Methylparaben | 0.10 |
| Tetrasodium EDTA | 0.12 |
| Triethanolamine | 0.50 |
| Lecithin | 5.00 |
| Behenyl Alcohol | 1.00 |
| Stearic Acid | 0.10 |
| Sodium Hyaluronate | 0.01 |
| Glyceryl Stearate | 1.00 |
| C12-16 Alcohols | 1.00 |
| Germall II | 0.30 |
| Palmitic Acid | 1.00 |
| Bisabolol | 0.10 |
| Polysorbate - 20 | 0.20 |
| 90% Polyphenol Green Tea Extract | 0.25 |
| Cucumber Extract | 1.00 |
| Chamomile Extract | 0.10 |
| Soy Phospholipids | 0.25; | b. topically applying said composition to the skin to be treated; and
   c. periodically repeating said topical application.

4. A method of treating acne rosacca of the skin by topical application, consisting essentially of the steps of:
   a. preparing a composition for topical application containing a therapeutically effective amount of at least one polyphenol derived from green tea dispersed in a suitable dermatologically acceptable vehicle, said composition comprising a serum having the following ingredients present in the below-listed percentage by weight:

| Ingredient | % |
| --- | --- |
| Water | 96.92 |
| Carbomer | 0.40 |
| Methylparaben | 0.10 |
| Tetrasodium EDTA | 0.12 |
| Triethanolamine | 0.50 |
| Sodium Hyaluronate | 0.01 |
| Germall II | 0.30 |
| Bisabolol | 0.10 |
| Polysorbate - 20 | 0.20 |
| 90% Polyphenol Green Tea Extract | 0.25 |
| Cucumber Extract | 1.00 |
| Chamomile Extract | 0.10; | b. topically applying said composition to the skin to be treated; and
   c. periodically repeating said topical application.

5. A method of treating skin surface irregularities and acne scars in skin by topical application, consisting essentially of the steps of:
   a. preparing a composition for topical application containing a therapeutically effective amount of at least one polyphenol derived from green tea dispersed in a suitable dermatologically acceptable vehicle, said composition comprising a serum having the following ingredients present in the below-listed percentage by weight:

| Ingredient | % |
| --- | --- |
| Water | 87.57 |
| Carbomer | 0.40 |
| Methylparaben | 0.10 |
| Tetrasodium EDTA | 0.12 |
| Triethanolamine | 0.50 |
| Lecithin | 5.00 |
| Behenyl Alcohol | 1.00 |
| Stearic Acid | 0.10 |
| Sodium Hyaluronate | 0.01 |
| Glyceryl Stearate | 1.00 |
| C12-16 Alcohols | 1.00 |
| Germall II | 0.30 |
| Palmitic Acid | 1.00 |
| Bisabolol | 0.10 |
| Polysorbate - 20 | 0.20 |
| 90% Polyphenol Green Tea Extract | 0.25 |
| Cucumber Extract | 1.00 |
| Chamomile Extract | 0.10; |
| Soy Phospholipids | 0.25; | b. topically applying said composition to the skin to be treated; and
   c. periodically repeating said topical application.

6. A method of treating skin surface irregularities and acne scars in skin by topical application, consisting essentially of the steps of:
   a. preparing a composition for topical application containing a therapeutically effective amount of at least one polyphenol derived from green tea dispersed in a suitable dermatologically acceptable vehicle, said composition comprising a serum having the following ingredients present in the below-listed percentage by weight:

| Ingredient | % |
| --- | --- |
| Water | 96.92 |
| Carbomer | 0.40 |
| Methylparaben | 0.10 |
| Tetrasodium EDTA | 0.12 |
| Triethanolamine | 0.50 |
| Sodium Hyaluronate | 0.01 |
| Germall II | 0.30 |
| Bisabolol | 0.10 |
| Polysorbate - 20 | 0.20 |
| 90% Polyphenol Green Tea Extract | 0.25 |
| Cucumber Extract | 1.00 |
| Chamomile Extract | 0.10; | b. topically applying said composition to the skin to be treated; and c. periodically repeating said topical application.

7. A method of treating hyper-pigmentation melasma of the skin by topical application, consisting essentially of the steps of:

a. preparing a composition for topical application containing a therapeutically effective amount of at least one polyphenol derived from green tea dispersed in a suitable dermatologically acceptable vehicle, said composition comprising a cream having the following ingredients present in the below-listed percentage by weight:

| Ingredient | % |
| --- | --- |
| Water | 87.57 |
| Carbomer | 0.40 |
| Methylparaben | 0.10 |
| Tetrasodium EDTA | 0.12 |
| Triethanolamine | 0.50 |
| Lecithin | 5.00 |
| Behenyl Alcohol | 1.00 |
| Stearic Acid | 0.10 |
| Sodium Hyaluronate | 0.01 |
| Glyceryl Stearate | 1.00 |
| C12-16 Alcohols | 1.00 |
| Germall II | 0.30 |
| Palmitic Acid | 1.00 |
| Bisabolol | 0.10 |
| Polysorbate - 20 | 0.20 |
| 90% Polyphenol Green Tea Extract | 0.25 |
| Cucumber Extract | 1.00 |
| Chamomile Extract | 0.10 |
| Soy Phospholipids | 0.25; | b. topically applying said composition to the skin to be treated; and c. periodically repeating said topical application.

8. A method of treating hyper-pigmentation melasma of the skin by topical application, consisting essentially of the steps of:

a. preparing a composition for topical application containing a therapeutically effective amount of at least one polyphenol derived from green tea dispersed in a suitable dermatologically acceptable vehicle, said composition comprising a serum having the following ingredients present in the below-listed percentage by weight:

| Ingredient | % |
| --- | --- |
| Water | 96.92 |
| Carbomer | 0.40 |
| Methylparaben | 0.10 |
| Tetrasodium EDTA | 0.12 |
| Triethanolamine | 0.50 |
| Sodium Hyaluronate | 0.01 |
| Germall II | 0.30 |
| Bisabolol | 0.10 |
| Polysorbate - 20 | 0.20 |
| 90% Polyphenol Green Tea Extract | 0.25 |
| Cucumber Extract | 1.00 |
| Chamomile Extract | 0.10; | b. topically applying said composition to the skin to be treated; and c. periodically repeating said topical application.

9. A topically applied composition for treating fine lines and wrinkles in skin, acne rosacea, surface irregularities of the skin and hyperpigmentation melasma of the skin consisting essentially of at least one polyphenol compound derived from green tea dispensed in a suitable dermatologically acceptable vehicle, said composition comprises a cream having the following ingredients with said ingredients being provided in the below listed percentage by weight:

| Ingredient | % |
| --- | --- |
| Water | 87.57 |
| Carbomer | 0.40 |
| Methylparaben | 0.10 |
| Tetrasodium EDTA | 0.12 |
| Triethanolamine | 0.50 |
| Lecithin | 5.00 |
| Behenyl Alcohol | 1.00 |
| Stearic Acid | 0.10 |
| Sodium Hyaluronate | 0.01 |
| Glyceryl Stearate | 1.00 |
| C12-16 Alcohols | 1.00 |
| Germall II | 0.30 |
| Palmitic Acid | 1.00 |
| Bisabolol | 0.10 |
| Polysorbate - 20 | 0.20 |
| 90% Polyphenol Green Tea Extract | 0.25 |
| Cucumber Extract | 1.00 |
| Chamomile Extract | 0.10 |
| Soy Phospholipids | 0.25. |

10. A topically applied composition for treating fine lines and wrinkles in skin, acne rosacea, surface irregularities of the skin and hyperpigmentation melasma of the skin consisting essentially of at least one polyphenol compound derived from green tea dispensed in a suitable dermatologically acceptable vehicle, said composition comprising a serum having the following ingredients present in the below-listed percentage by weight:

| Ingredient | % |
| --- | --- |
| Water | 96.92 |
| Carbomer | 0.40 |
| Methylparaben | 0.10 |
| Tetrasodium EDTA | 0.12 |
| Triethanolamine | 0.50 |
| Sodium Hyaluronate | 0.01 |
| Germall II | 0.30 |

-continued

| Ingredient | % |
|---|---|
| Bisabolol | 0.10 |
| Polysorbate - 20 | 0.20 |
| 90% Polyphenol Green Tea Extract | 0.25 |

-continued

| Ingredient | % |
|---|---|
| Cucumber Extract | 1.00 |
| Chamomile Extract | 0.10. |

* * * * *